United States Patent
Weyne et al.

(10) Patent No.: US 9,926,241 B2
(45) Date of Patent: Mar. 27, 2018

(54) CATALYST BED SYSTEM FOR AN ENDOTHERMIC CATALYTIC DEHYDROGENATION PROCESS AND AN ENDOTHERMIC DEHYDROGENATION PROCESS

(71) Applicant: Borealis AG, Vienna (AT)

(72) Inventors: Kristof Weyne, Ghent (BE); Guhan Mathivanan, Linz (AT)

(73) Assignee: Borealis AG, Vienna (AT)

( * ) Notice: Subject to any disclaimer, the term of this patent is extended or adjusted under 35 U.S.C. 154(b) by 523 days.

(21) Appl. No.: 14/353,619

(22) PCT Filed: Oct. 22, 2012

(86) PCT No.: PCT/EP2012/070860
§ 371 (c)(1),
(2) Date: Apr. 23, 2014

(87) PCT Pub. No.: WO2013/060640
PCT Pub. Date: May 2, 2013

(65) Prior Publication Data
US 2014/0296606 A1 Oct. 2, 2014

(30) Foreign Application Priority Data
Oct. 24, 2011 (EP) .................................. 11186322

(51) Int. Cl.
*C07C 5/333* (2006.01)
*B01J 8/04* (2006.01)
(Continued)

(52) U.S. Cl.
CPC ............. *C07C 5/3332* (2013.01); *B01J 8/025* (2013.01); *B01J 8/0285* (2013.01); *B01J 8/0292* (2013.01);
(Continued)

(58) Field of Classification Search
CPC ..... C07C 5/3332; C07C 5/3335; B01J 8/0446; B01J 8/0492; B01J 2208/00513; B01J 2208/00522
(Continued)

(56) References Cited

U.S. PATENT DOCUMENTS 2,419,997 A 5/1947 Houdry
4,560,824 A 12/1985 Spence et al.
(Continued)

FOREIGN PATENT DOCUMENTS

CN 1675146 A 9/2005
CN 101734987 A 6/2010
(Continued)

OTHER PUBLICATIONS

Estridge, B.H.; Reynolds, A.P.; Walters, J. "Basic Medical Laboratory Techniques, 4th Ed."; Delmar: London, UK (2000), p. 78.*

*Primary Examiner* — Philip Louie
*Assistant Examiner* — Aaron Pierpont
(74) *Attorney, Agent, or Firm* — The Webb Law Firm

(57) ABSTRACT

A catalyst bed system, and a dehydrogenation process using the same, including a horizontal catalyst bed having a mixture of at least one catalytic material and at least one first inert material, a predetermined volume of at least one second inert material arranged upstream of the catalyst bed, wherein the volume of the reactor above the catalyst bed system is not filled by any solid material (empty space). The volume of the second inert material and the volume of the reactor above the second inert material (empty space) is between 0.04 and 0.73, preferably between 0.06 and 0.3, most preferably between 0.09 and 0.2.

4 Claims, 4 Drawing Sheets

(51) Int. Cl.
  *B01J 8/02* (2006.01)
  *B01J 23/26* (2006.01)
(52) U.S. Cl.
  CPC .......... *B01J 8/0419* (2013.01); *B01J 8/0496* (2013.01); *C07C 5/3335* (2013.01); *B01J 23/26* (2013.01); *B01J 2208/00522* (2013.01); *C07C 2521/04* (2013.01); *C07C 2523/26* (2013.01); *Y02P 20/52* (2015.11)
(58) Field of Classification Search
  USPC .................. 585/654, 661, 602, 636; 422/216
  See application file for complete search history.

(56) References Cited

U.S. PATENT DOCUMENTS

| | | | |
|---|---|---|---|
| 5,510,557 A * | 4/1996 | Gartside | ............... C07B 35/04 208/34 |
| 6,392,113 B1 | 5/2002 | Gartside | |
| 7,566,429 B2 | 7/2009 | Buelna et al. | |
| 2003/0139637 A1* | 7/2003 | Rytter | ............... B01J 8/0278 585/658 |
| 2006/0004241 A1 | 1/2006 | Schindler et al. | |
| 2006/0281958 A1* | 12/2006 | Buelna | ............... B01D 3/009 422/211 |
| 2007/0054801 A1* | 3/2007 | Fridman | ............... B01J 23/26 502/318 |
| 2008/0045685 A1* | 2/2008 | Dieterle | ............... B01J 8/0453 526/328 |
| 2008/0097134 A1* | 4/2008 | Fridman | ............... B01J 23/26 585/899 |

FOREIGN PATENT DOCUMENTS

| | | |
|---|---|---|
| GB | 1074129 | 6/1967 |
| WO | 9523123 A1 | 8/1995 |
| WO | 2006124145 A1 | 11/2006 |
| WO | 2007018982 A1 | 2/2007 |
| WO | 2007030298 A1 | 3/2007 |

* cited by examiner

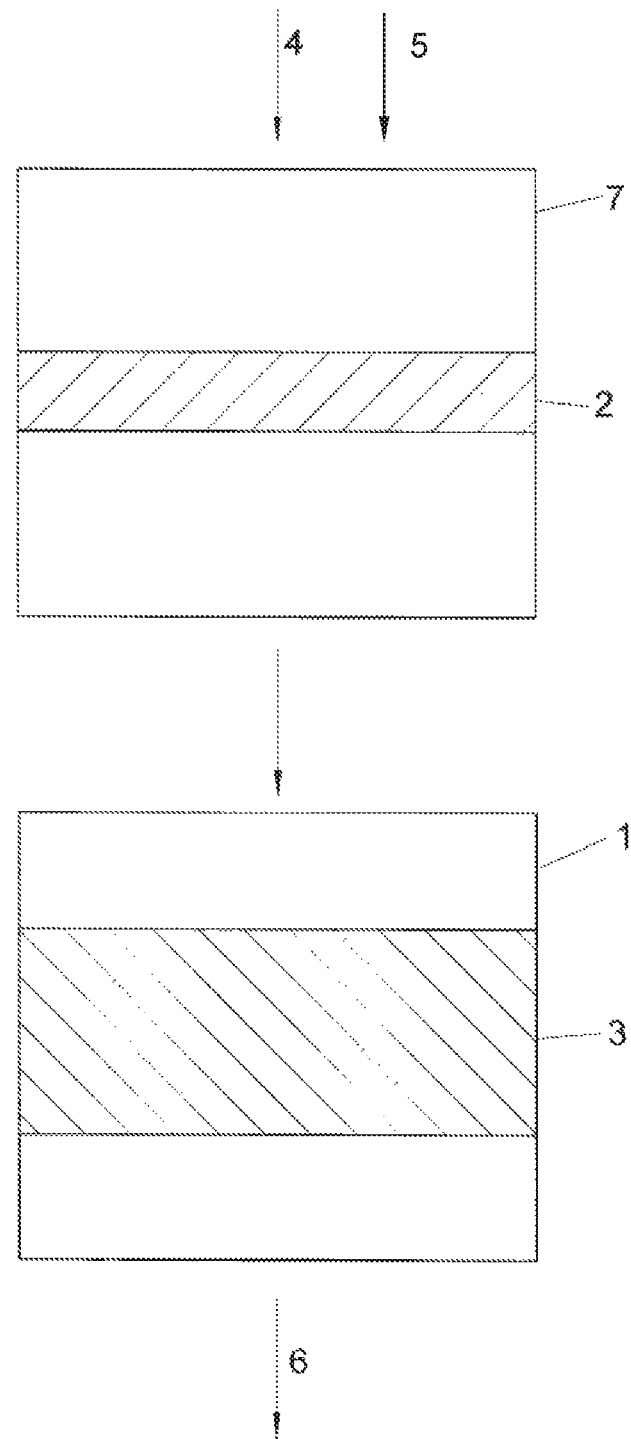

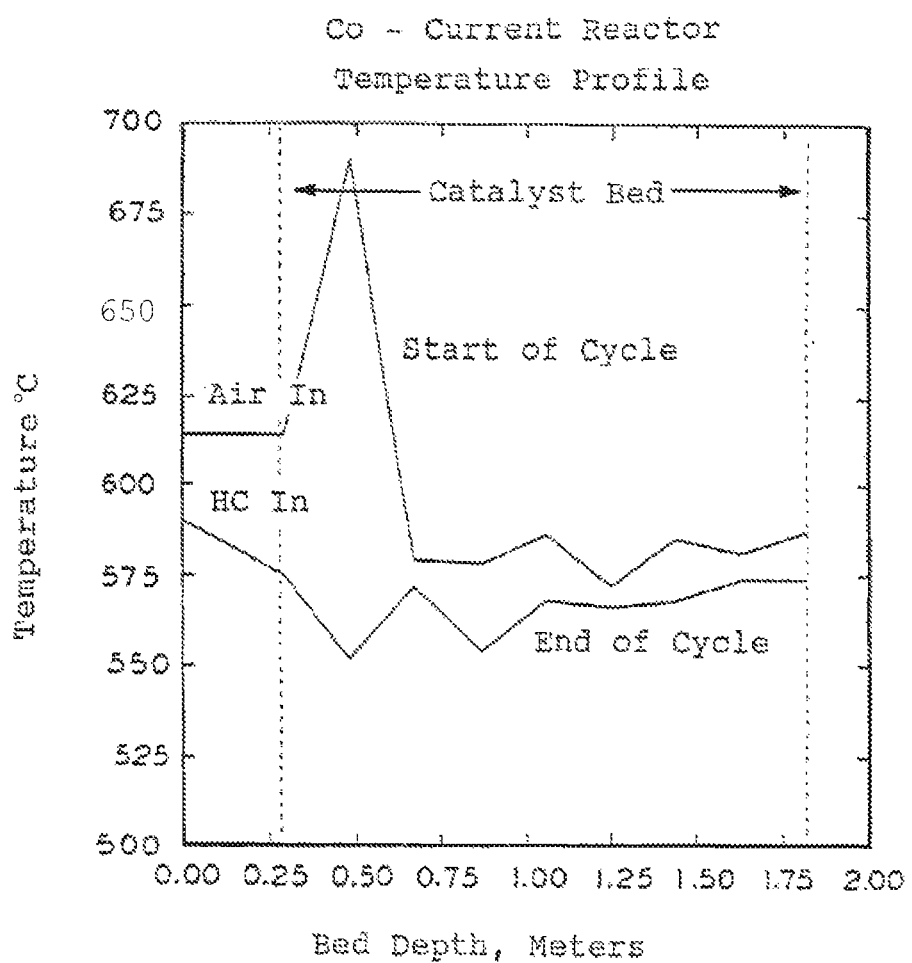

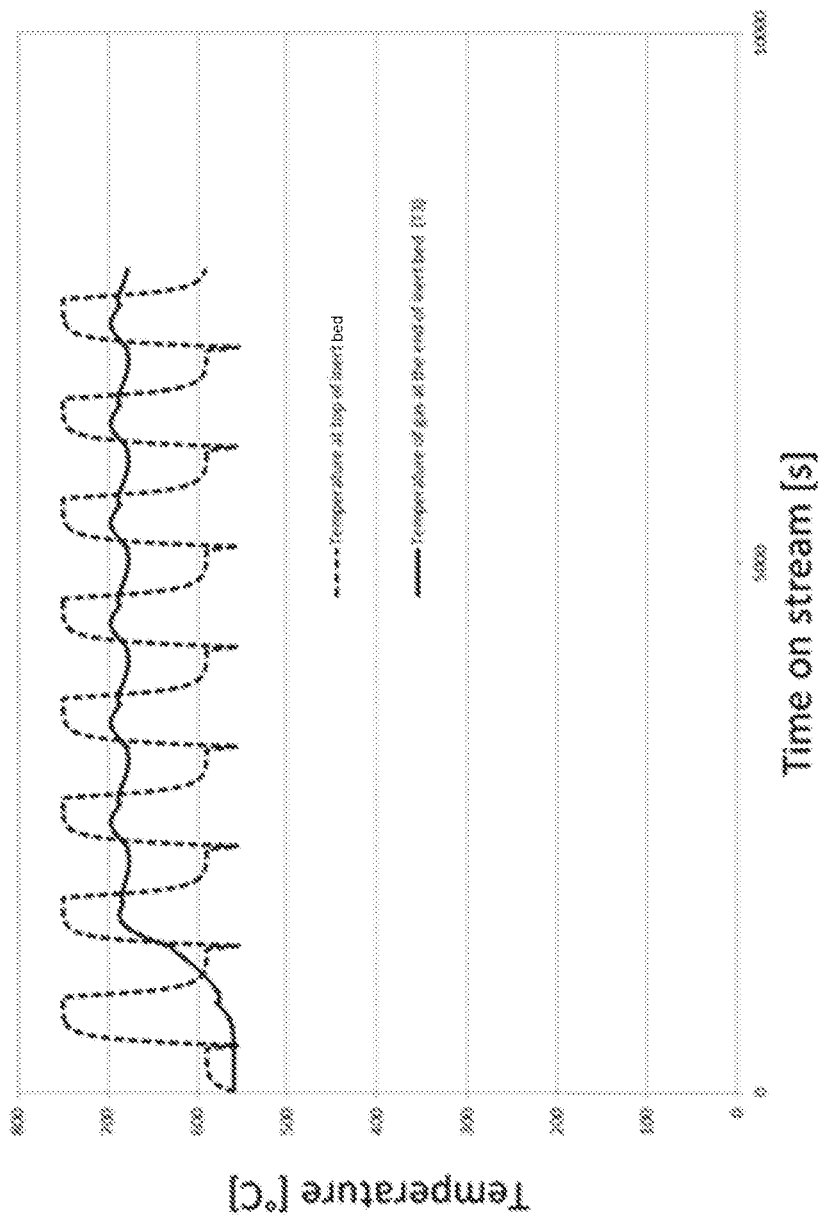

CATALYST BED SYSTEM FOR AN ENDOTHERMIC CATALYTIC DEHYDROGENATION PROCESS AND AN ENDOTHERMIC DEHYDROGENATION PROCESS

CROSS-REFERENCE TO RELATED APPLICATIONS

This application is the United States national phase of International Application No. PCT/EP2012/070860 filed Oct. 22, 2012, and claims priority to European Patent Application No. 11186322.1 filed Oct. 24, 2011, the disclosures of which are hereby incorporated in their entirety by reference.

BACKGROUND

The present invention relates to a catalyst bed system for an endothermic dehydrogenation process and an endothermic dehydrogenation process using said catalyst bed system.

The invention is concerned with an endothermic hydrocarbon process, particularly for adiabatic catalytic dehydrogenation of paraffinic and other hydrocarbons such as propane dehydrogenation (reaction 1) or butane dehydrogenation (reaction 2):

$$C_3H_8 \rightleftharpoons C_3H_6 + H_2 \quad (1)$$

$$C_4H_{10} \rightleftharpoons C_4H_6 + 2H_2 \quad (2)$$

Dehydrogenation of hydrocarbons, in particular aliphatic hydrocarbons, to convert them into their respective olefins is a well known process. For example, the hydrocarbons propane, butane, isobutane, ethyl benzene are well known and catalytically dehydrogenated to produce the respective propylene, butene, isobutene, butadiene and styrene. Dehydrogenation reactions are strongly endothermic and thus, an increase of the heat supply favours the olefin conversion.

One well known dehydrogenation process is the Houdry CATOFIN® process in which an aliphatic hydrocarbon is passed through a dehydrogenation catalyst bed where the hydrocarbon is dehydrogenated to the respective olefin, the olefin is flushed from the bed, the catalyst is regenerated and reduced, and the cycle is repeated (U.S. Pat. No. 2,419,997).

Another well known process is the CATADIENE® process in which butanes and butenes are dehydrogenated to produce butadiene. This process is again a cyclic process, similar to the previous mentioned CATOFIN® process.

Typically the catalyst is heated by contact with a heated gas, usually air. The aliphatic hydrocarbon such as propane is passed through the hot catalyst bed which supplies the heat for the dehydrogenation reaction. Since the dehydrogenation reaction is endothermic and the process is adiabatic, the temperature of the catalyst gradually drops during the dehydrogenation cycle and causes a decrease in hydrocarbon conversion rate. Particularly the temperature at the top of the catalyst bed decreases by as much as 100° C. (US 2007/0054801 A1).

In order to reheat the catalyst bed and remove coke that has deposited on the catalyst during the dehydrogenation step, the reactor is purged of hydrocarbon and undergoes a regeneration step with air heated to temperatures up to 700° C. Heat is provided to the bed by the hot air that passes through the bed and also by the combustion of coke deposits on the catalyst. After reheating and regenerating the catalyst and before putting the reactor back on stream, the oxidized catalyst must be reduced by passing a reduction gas such as hydrogen or hydrocarbon through the catalyst bed. This also supplies additional heat by the oxidation of the reducing gas (US 2007/0054801 A1).

The question of additional heat supply to the reactor bed in order to compensate for the heat consumption during the strong endothermic reaction has been addressed in the past and different approaches have been suggested.

For instances U.S. Pat. No. 6,392,113 B1 proposes to react the hydrocarbon feed partially in a catalytic pre-reactor and reheating the exiting hydrocarbon stream from pre-reactor to the same preheat temperature prior to introduction into the main catalytic reactor. Reheating can be done either by exiting regeneration air or by a separately fired heater.

WO2007/030298 A1 describes an improved catalyst bed system. In one part of the catalyst bed, the propane dehydrogenation catalyst is mixed with any inert material which does not produce heat during the whole process and in another part of the bed, propane dehydrogenation catalyst along with normal inert material, a new material which is catalytically inert with respect to dehydrogenation, cracking, coking reactions and generates heat when it is exposed to reducing and/or oxidizing reaction conditions.

US2006/0004241 A1 discloses a way to decrease the temperature gradient in isothermal propane dehydrogenation process. This patent proposes to dilute the catalyst bed with inert particles at the beginning of the catalyst bed to decrease the temperature gradient in the section of catalyst bed for the isothermal propane dehydrogenation process.

WO2007/018982 A1 uses two different catalyst zones for adiabatic, non-oxidative hydrocarbon dehydrogenation processes. The first zone of catalyst has higher activity and higher capacity to produce more coke than the second layer. The combustion of coke in turn provides extra heat.

A similar approach is applied by U.S. Pat. No. 4,560,824 A, which proposes additional heat by increasing coke production. The coke production is caused by adding unsaturated components to the feed during dehydrogenation.

As can be seen from the prior art there are several possibilities to increase the heat during the dehydrogenation process, in particular by increasing the hydrocarbon feed temperature, increasing air inlet temperature and increasing air flow rate. Additional heat can also be provided by injecting and combusting a fuel gas with regeneration air and increasing flow rate of said injection gas.

However, there are several challenges associated with the above described possibilities.

An increase of temperature of the hydrocarbon feed could create cracking of hydrocarbons to lighter products and coking in the pipelines. An increase of the air inlet temperature or injection gas flow rate in order to increase the temperature in the catalyst layer could accelerate catalyst deactivation. Furthermore, once designed, a plant runs to the limit of air handling equipment. Increasing air flow requires major capital expenditures (U.S. Pat. No. 6,392,113 B1).

SUMMARY

Thus, it would be advantageous to provide a method to add additional heat to the aliphatic dehydrogenation process without having the above described drawbacks.

According to an exemplary embodiment of the invention, a catalyst bed system for use in a reactor in an endothermic dehydrogenation process is provided, which comprises
- a horizontal catalyst bed comprising a mixture of at least one catalytic material and at least one first inert material, a predetermined volume of at least one second inert material arranged upstream of the catalyst bed, wherein the volume of the reactor above the catalyst bed system including the second inert material is not filled by any solid material, i.e. the reactor comprises an empty space above the catalyst bed system. This means that the second inert material layer as part of the catalyst bed system, which is arranged upstream of the catalyst bed does not completely fill the remaining reactor volume above the catalytic bed and thus does not have any support function.

The catalytic bed system according to the invention is characterized in that the ratio of the volume of the second inert material and the volume of the reactor above the catalyst bed system and thus above the second inert material (empty space) is between 0.04 and 0.73, preferably between 0.06 and 0.3, most preferably between 0.09 and 0.2. This means that the volume of second inert material used is always smaller than the empty space volume. i.e. the volume of the reactor above the second inert material.

It should be noted that the volume of the second inert material includes the material as such but also possible pores filled with air between the inert layer particles.

According to the invention the second layer of inert material is being arranged upstream of the catalytic bed. This can be done in multiple ways.

One preferred arrangement is that the layer of a second inert material is disposed on top or on the upper surface of the catalyst bed which is usually arranged in a horizontal manner. The layer of second inert material and the catalytic material are in direct contact with each other.

Thus, in an exemplary embodiment of the present catalyst bed system the predetermined volume of the second inert material is a layer disposed on top or the upper surface of the catalyst bed. In such a case the layer of the second inert material may have approximately a thickness D in a range between 10 cm and 100 cm, preferably 15 cm and 60 cm, most preferably between 20 and 40 cm. A thickness of the second inert material layer of 10 cm to 100 cm would correspond for instance to a ratio of second inert material volume to empty space from 0.04 to 0.73, a thickness of the second inert material layer of 15 cm to 60 cm would correspond to a ratio of second inert material volume to empty space from 0.06 to 0.3, and a thickness of the second inert material layer of 20 cm to 40 cm would correspond to a ratio of second inert material volume to empty space from 0.09 to 0.2.

Another possible arrangement is that the second inert material is arranged in an extra vessel which is upstream of the reactor. Thus, the layer of second inert material and the catalytic material are not in direct contact with each other; they are rather spatially separated.

Thus, in another exemplary embodiment of the present catalyst bed system the predetermined volume of the second inert material is arranged in at least one extra vessel, which is arranged upstream of the reactor. In this case the volume of the second inert material in the at least one vessel may be between 15 and 180 tons, preferably 20 and 110 tons and most preferably 30 and 70 tons.

In a further exemplary embodiment the present catalyst bed system comprising a horizontal catalyst bed as a mixture of catalytic material and a first inert material for use in an endothermic dehydrogenation process is provided, wherein in said process optionally a reduction gas is fed for reducing the catalytic material, a heat stream having a first temperature $T1$ for heating and/or regenerating the catalytic material is fed into reactor comprising the catalyst bed system and subsequently a hydrocarbon stream having a second temperature $T2$ is fed into the reactor comprising the catalyst bed system, wherein $T1>T2$.

This means that the temperature $T1$ for heating and regenerating the catalytic material is usually by 50 to 140° C. higher than the temperature $T2$ of the hydrocarbon feed.

Furthermore, the heat stream preferably comprises a hot air stream or air feed and an injection gas feed. Thus, temperature $T1$ of the heat stream is preferably the temperature resulting from the combustion of air and injection gas. It is however in general conceivable to increase the heat input also by other measures. For instance, heat can be provided in a direct manner such as by combustion of fuel gas or in an indirect manner by heating air without combustion gas. It is furthermore conceivable to increase the heat input into the catalytic bed also by measures such as heating the reactor mantle. That means heating measures from the inside or the outside of the reactor are possible. It is also conceivable to add the heat within the reactor or before air enters the reactor.

The catalyst bed system according to the invention comprises a layer of a second inert material being arranged upstream of the catalyst bed, wherein the thickness D of the volume of the second inert material, i.e. layer of the second inert material and/or the amount of the second inert material is chosen such that an almost constant temperature $T3$, i.e. a temperature $T3$ with no or little fluctuation at the interface of the second inert material and the catalyst bed is obtained being $T1>T3>T2$.

"Interface of the second inert material and the catalyst bed" within the meaning of the present invention means therefore not only the area of direct contact between second inert material and catalyst bed, but can also mean that the second inert material and catalyst bed are in indirect contact with each other and are rather connected via a gas communication due to the heat stream and hydrocarbon stream.

By providing an extra layer of a second inert material upstream of the catalyst bed, such as on top of the catalyst bed it was surprisingly found that a constant temperature $T3$ at the interface of said layer and the catalyst bed or at the outlet of said layer to the catalyst bed could be provided wherein said temperature $T3$ has a value which is between temperature $T1$ of the heat stream and temperature $T2$ of the hydrocarbon stream. The extra inert layer is thus able to buffer the different feed temperatures, such as in case of an increased heat input.

Thus, it is now possible to provide additional heat for the process without exposing the catalyst to its maximum allowed temperature. Also installation of such a pure inert layer reduces the temperature fluctuation at the top catalyst zone.

The extra inert layer stores heat during the regeneration phase and releases it by preheating the propane during the dehydrogenation phase. While storing the heat, the temperature at the outlet of that layer and thus at the inlet of the catalyst bed beneath the layer or the interface of both layers is buffered, resulting in a higher heat input with the same catalyst exposure temperatures or lower and more even catalyst exposure temperatures with the same heat input. In between both cases, it is thus also possible to reduce maximum exposure temperatures in the catalyst bed with increasing average catalyst temperature.

By adding an extra layer of inert material on top of the catalyst bed the catalyst bed is more isothermal and allows for an increase in olefin production by using two operational modes. Furthermore, when using a second inert material arranged upstream of the catalyst bed made of catalytic material and first inert material allows a faster start-up of the process, i.e. an increased stability at the beginning of the process compared to a conventional set up.

In a first operational mode the heat input is increased by adding more heat such as in way of more injection gas during regeneration. The heat increase results in a higher hydrocarbon conversion such as propane conversion and thus contributes to a higher olefin production, such for instance propylene production.

In a second operational mode the heat input is kept on a constant level and thus a strong temperature drop within the catalyst bed is avoided due to the extra layer of inert material. By providing constant although lower operating temperatures the selectivity of the desired olefin such as propylene, isobutene and butadiene increases and thus the overall yield increases. The higher selectivity due to the extra layer of inert material is also accompanied by a longer catalyst life time and longer periods between plant turn-arounds and catalyst exchange or replacement.

Independent of the two operational modes in respect to higher selectivity or higher conversion rate, the specific energy consumption decreases significantly, that means GJ/ton olefin such as propylene produced. More olefin such as propylene is produced with a same amount of hydrocarbon feed such as propane feed in case of either operating at higher selectivity or by increasing the heat as for instance by adding extra injection gas. Of course it is also possible to combine the described two modes of operation, i.e. with higher selectivity and higher conversion when using the present catalyst bed system.

The temperature T1 of the heat stream consisting of hot air and injection gas can be in a range between 600 an 1000° C., preferably between 700 and 900° C. and most preferably between 725 and 810° C.

The temperature T2 of the hydrocarbon stream can be in a range between 400 and 650° C., preferably 550 and 650° C.

In an exemplary embodiment of the present catalyst bed system the temperature T3 at the outlet of the second inert material volume/layer into the catalyst bed or the interface of said second inert layer and the catalyst bed does not exceed a temperature at which the deactivation of the catalytic material is being accelerated. Thus, the catalytic material is solely exposed to a maximum exposure temperature which is in general depending on the catalytic material being used in the dehydrogenation process.

It is preferred, that the temperature T3 is between 500 and 800° C., preferably between 550 and 750° C.

It is preferred, if the temperature T3 fluctuates at most about 10 to 100° C., preferably about 20 to 80° C., most preferred about 30 to 60° C.

Suitable materials which can be used as inert material layer upstream of the catalyst bed are for example, the oxides of elements of main groups II, III and IV, transition groups III, IV and V and also mixtures of two or more of these oxides, and also nitrides and carbides of elements of main groups III and IV. Typical examples are magnesium oxide, aluminum oxide, silicon dioxide, steatite, titanium dioxide, zirconium dioxide, niobium oxide, thorium oxide, aluminum nitride, silicon carbide, magnesium silicates, aluminum silicates, clay, kaolin and pumice. The second inert material is preferably selected from the group of aluminum oxide, aluminas, alumina monohydrate, alumina trihydrate, alumina-silica, transition aluminas, alpha-alumina, silica, silicate, aluminates, calcined hydrotalcites, zeolites and combinations thereof. Alumina is in particular preferred.

In the context of the present invention "inert material" is defined as a material which does not exhibit any catalytic effect in the dehydrogenation reaction, but may participate in other reactions such as cracking or coking which take place during dehydrogenation.

The catalytically inactive second inert material has preferably a low BET surface area. This is generally <10 m$^2$/g, preferably <5 m$^2$/g, and particularly preferably <1 m$^2$/g. A low BET surface area can be obtained by ignition of the abovementioned oxides or ceramic materials at high temperatures of, for example, >1 000° C.

The second inert material has preferably a coefficient of thermal conduction at 293 K of >0.04 W/(mK), preferably >0.4 W/(mK) and particularly preferably >2 W/(mK).

The second inert material can be used in the form of crushed material or shaped bodies. The inert material used as the top layer can be in the form of crushed particles. Sizes can be spheres, grains and extrudates. Typically the particle sizes, in particular the diameter of the second inert material is between at least 2 mm.

The proportion of void fraction within the layer of the second inert material is preferably at least 20%, more preferably from 30 to 70%, particularly preferably from 40 to 70%.

The catalyst bed comprises preferably 50 Vol % of a catalytic material and 50 Vol % of a first inert material. However, in case of isobutane dehydrogenation 70 Vol % catalytic materials is mixed with 30 Vol % inert materials (see US 2007/054801 A1).

The catalytic material is preferably selected from a group consisting of chromium oxide, zirconium oxide or a mixture thereof. The first inert material is preferably selected from the group consisting of magnesium oxide, aluminium oxide, aluminium nitride, titanium oxide, zirconium dioxide, niobium oxide, aluminium silicate and others.

A typical Chromium oxide dehydrogenation catalyst manufactured on an alumina support comprises from about 17 wt % to about 22 wt % $Cr_2O_3$. These types of dehydrogenation catalyst are known for instance under the name Catofin® Standard catalyst (US 2008/0097134 A1). It is to be understood that the concept of the present process—namely the use of an extra inert layer—is applicable to any type of dehydrogenation catalyst and not only to the ones explicitly mentioned within the context of this application. Thus, all other commonly used dehydrogenation catalysts may also be applicable.

The first and the second inert material can be the same or different from each other.

The basic idea underlying the present invention is independent on the number of reactors used and the reactor cycles. The buffering effect is obtained for cycles having different lengths of dehydrogenation, regeneration and reduction phases.

As described above, it is conceivable to arrange the extra layer of a second inert material not only on the top of the catalyst bed but rather instead or additionally in a separate vessel. In such an embodiment the second inert material is filled in a separate vessel, wherein the metal surfaces thereof can be protected by refractory metal. The amount of inert material used in such a case can be between 15 and 180 tons, preferably 20 and 110 tons and most preferably 30 and 70 tons.

The catalyst bed is prepared by mixing or combining the catalytic material and the first inert material. The required amount of catalytic material is determined and is then mixed with a defined amount of first inert material. The catalyst bed is evacuated and reduced with hydrogen. Then an aliphatic hydrogen carbon such as propane, butane, isobutane or an aromatic hydrocarbon such as ethyl benzene is fed to the catalyst bed and is dehydrogenated upon contact with the catalytic material to the corresponding unsaturated hydrocarbons such as propylene, butadiene, isobutene or styrene.

Accordingly, an endothermic catalytic dehydrogenation process using a catalyst bed system as described above comprising a horizontal catalyst bed comprising a mixture of at least one catalytic material and at least one first inert material, a predetermined volume of at least one second inert material arranged upstream of the catalyst bed, wherein the volume of the reactor above the catalyst bed system is not filled by any solid material (empty space), and wherein the ratio of the volume of the second inert material and the volume of the reactor above the second inert material (empty space) is between 0.04 and 0.73, preferably between 0.06 and 0.3, most preferably between 0.09 and 0.2, comprises the following steps:
  opt. passing a reduction gas through the volume of the second inert material being on top of the catalyst bed and the catalyst bed consisting of catalytic material and a first inert material for reducing the catalytic material,
  passing a heat stream having a first temperature T1 through the volume of the second inert material and the catalyst bed and thereby heating the second inert material and the catalyst bed and regenerating the catalytic material within the catalyst bed,
  passing a hydrocarbon stream having a second temperature T2 through the volume of the second inert material and the catalyst bed and thereby dehydrogenating the hydrocarbon in the catalyst bed,
  wherein T1>T2, and
  wherein the temperature T3 at the interface of the second inert material and the catalyst bed is T1>T3>T2.

In an exemplary embodiment the temperature T1 of the heat stream is between 600 and 1000° C., preferably between 700 and 900° C., most preferably between 725 and 810° C.

It is thereby preferred that the heat stream comprises hot air stream and injection gas stream as for instance a fuel gas stream.

The hot air stream may be fed at a rate between 100 and 500 Mt/hr, preferably between 150 and 400 Mt/hr, most preferably between 200 and 300 Mt/hr, whereby 210 Mt/hr is the typical applied feed rate.

The injection gas stream can be fed with a rate between 0.1 and 0.6 kg/sec preferably between 0.1 and 0.4 kg/sec, most preferably between 0.1 and 0.2 kg/sec, whereby 0.125 kg/sec is the typical fed rate. Thereby the fed rate of the injection gas stream depends strongly on the operational mode as described above.

If the production process is to be conducted with an increased heat input according to the first operational mode then the rate of injection gas stream may be increased. The heat increase allows for a higher olefin production without exposing the catalytic material to higher temperatures due to the extra inert material layer which would otherwise inactivate the catalytic material.

If the production process on the other hand is to be conducted when using the present catalyst bed system at the same conventional operating parameters according to the second operational mode then the rate of injection gas stream may not be changed. This allows for the same heat input with lower, but more even catalyst exposure temperatures and a higher selectivity and longer catalyst life time.

In another exemplary embodiment of the present process the temperature T2 of the hydrocarbon stream is between 400 and 650° C., preferably between 550 and 650° C.

The hydrocarbon stream may be fed at a rate between 20 and 60 Mt/hr, preferably between 25 and 50 Mt/hr, most preferably between 30 and 45 Mt/hr.

The ratio of air flow rate to hydrocarbon flow rate is typically in the range between 4:1 to 10:1.

It is preferred, if the temperature T3 is between 500 and 800° C., preferably between 550 and 750° C.

In general the present process may be conducted at a pressure in a range between 100 mmHg to 750 mmHg.

The present catalyst bed and process are not solely restricted to the described conditions. For instance the kind, shape and size of the inert material can be chosen in a very general manner. The present invention is applicable for all endothermic processes, but in particular for all dehydrogenation processes. The present invention is furthermore independent of the specific composition such as kind of material, ratio of different materials and thickness of the catalytic layer. The second inert material being used can be applied at all temperatures, and flows.

Furthermore, the present process does not depend on a specific reactor cycle and on the amount of reactors being used. Thus, the present process can be used in all dehydrogenation cycle lengths, regeneration cycle lengths and/or reduction phase length.

BRIEF DESCRIPTION OF THE DRAWINGS

The present invention is further explained in more detail based on the following examples in conjunction with the Figures.

FIG. 2 shows a schematic view of a second embodiment of the catalyst bed system according to the invention.

FIG. 3 shows a first diagram showing the temperature profile of a conventional catalytic bed and process.

FIG. 4 shows a second diagram showing the temperature profile of an embodiment of the catalytic bed and process according to the invention.

DETAILED DESCRIPTION

Figure 1:
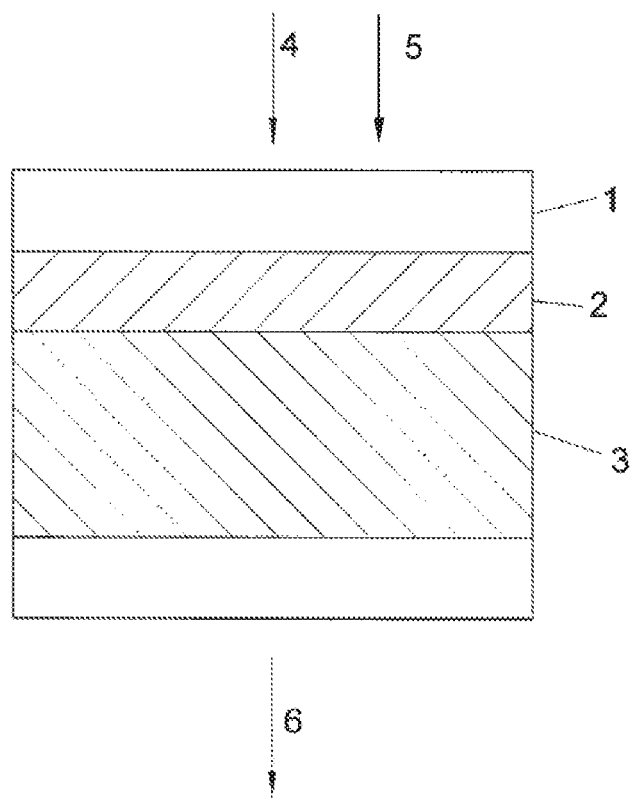
FIG. 1 shows a schematic view of a first embodiment of the catalyst bed system according to the invention.

FIG. 1 shows schematically a first embodiment of a set up of the catalytic bed. Here a reactor 1 for conducting a dehydrogenation process having a catalyst bed 3 and a layer of inert material 2 arranged thereon is illustrated.

In propane dehydrogenation (PDH) the horizontal catalyst bed 3 is a mixture of inert material and catalytic material with 50 vol % of each. The catalytic material is the active phase catalyzing the dehydrogenation while the inert phase stores the heat that it releases during the endothermic dehydrogenation reaction. Typically, a reaction cycle is a sequence of 7-15 min of hot regeneration air to heat up the catalyst bed and combust some coke and 7-15 min of propane dehydrogenation including with some side reactions like coke formation.

According to the present catalyst bed system the extra layer 2 of second inert material is arranged on top of the existing catalyst/inert material mixture. This extra layer 2 of inert material has a thickness of about 20 to 40 cm.

The heat stream 4 consisting of hot air and an injection fuel gas is fed to the catalyst bed system 2, 3 in order to heat and regenerate the catalyst system. Subsequently, a hydrocarbon feed in form of a propane feed 5 enters the reactor 1.

By flowing through the catalyst bed system 2 and 3 propane is dehydrogenated and the thus formed propene stream 6 leaves the reactor for further work up.

FIG. 2 shows schematically a second embodiment of an arrangement of the catalytic bed system according to the invention. Here a layer of inert material 2 is arranged in a separated vessel 7. Downstream of said vessel 7 the reactor 1 for conducting a dehydrogenation process having a catalyst bed 3 is arranged.

The amount of inert material in vessel 7 is 30 to 72 tons.

The heat stream 4 consisting of hot air and an injection fuel gas is fed at first to the vessel 7 passing the inert material layer 2 and subsequently to the catalyst bed 3 in order to heat and regenerate the catalyst system. Subsequently, a hydrocarbon feed in the form of a propane feed 5 enters vessel 7 and subsequently reactor 1. By flowing through the catalyst bed 3, propane is dehydrogenated and the thus formed propene/propylene stream 6 leaves the reactor for further work up.

FIG. 3 presents a temperature profile of a conventional process according to WO 95/23123 A1 not using an extra layer of inert material as the present process. Shown are the temperature profiles at the start of the hydrocarbon cycle and the end of the hydrocarbon cycle. The regeneration cycle restores the temperatures of the catalytic bed material. The temperature in the upper layers of the catalyst bed decreases sharply during the dehydrogenation cycle, as clearly can be seen from this temperature profile. This sharp temperature change can however be avoided when the reactor is operated with the second inert material as shown below.

Example 1: First Operational Mode—Additional Heat Input

According to the first operational mode using an arrangement according to FIG. 1 the injection gas flow is increased in order to provide extra heat.

Simulations of temperatures in the inert layer indicate that the outlet temperature at the bottom (outlet) of that layer can be almost constant and propane is heated to higher temperature than T2 during the dehydrogenation cycle.

In FIG. 4 a temperature profile of the catalytic bed for a first operational mode is shown. Here the gas outlet or interface temperature T3 (solid line) and gas inlet (dotted line) temperature T1, T2 of the inert layer, which has in this case a thickness of 40 cm, are presented over time. The inlet temperature of the inert layer—this means the temperature at the top of the layer—clearly reflects the sequential dehydrogenation (lower temperature T2) and regeneration phases (higher temperature T1) of a typical PDH unit operation in between regeneration and dehydrogenation.

The dehydrogenation phase is characterized by the propane feed at the lower temperature T2 and the regeneration phase is characterized by the heat feed at the higher temperature T1 representing the combined temperature of air and injection gas combustion (dotted line). In between the two phases, there is also a steam purge and reduction phase at lower temperatures. During the dehydrogenation cycle the top of the catalyst cools only down by 38° C. thus ensuring a relatively high overall temperature for the dehydrogenation cycle and an overall high conversion rate.

An increased heat input with the inert layer on top does not expose the catalytic material catalyst to temperatures higher than the maximum exposure temperature. In the embodiment as described here this maximum exposure temperature T3 of the catalytic material is between 550 and 700° C. It is however in general possible to apply other maximum exposure temperatures depending on the catalytic material.

The thickness of the extra layer of inert material has also an influence on the production rate.

In general, the propylene production increases using an extra layer of inert material upstream of the catalytic bed.

Conversion and selectivity data (not shown) indicate that the increase of propylene production is related to an increase in conversion rather than to a higher selectivity.

Furthermore, the coke production is also lower than in conventional batches (not shown).

There is furthermore no indication of a significant increase in cracking in the catalyst bed i.e. first inert material and/or catalyst material, when increasing the injection gas flow. This strongly indicates that at PDH operating temperatures thermal cracking is significantly lower than catalytic cracking.

In summary it is to be said that due to the arrangement of an extra layer of a second inert material on top of the conventional catalyst bed the propylene production can be increased significantly by adding extra heat for instance in form of extra injection gas. It is possible to add extra heat without exposing the catalyst to higher temperatures. This has a positive effect on selectivity and conversion.

Example 2: Second Operational Mode—Same Operating Conditions

The applicability of the present catalyst bed system using the same operating conditions i.e. no increased heat stream was also tested.

Propylene production in the present case and when using the conventional batch having the same heat input is higher in the first case using the extra layer of inert material on top of the catalyst bed. The production is increased.

When comparing the selectivity and conversion rate it interestingly can be stated that the conversion for both cases is similar. The higher production rate using the catalyst bed of the invention is rather due to an increased selectivity.

Higher selectivity is also confirmed by the lower coke production (not shown).

The inert layer is the main contributor for the higher selectivity in propylene production. It creates lower peak temperatures in the catalyst bed and that has a large effect on selectivity.

The average catalyst temperatures on the other hand do not differ much. In the batch using the catalytic system according to the invention the catalyst temperature seems to be a little bit lower because of the endothermic character of the dehydrogenation reaction. A higher production thus causes a lower average temperature.

In summary it can be said that when operating with the same process parameters, the extra inert layer provides a selectivity advantage resulting in extra propylene production.

Maximum temperature exposure of the catalyst bed is lower than in previous batches and the selectivity higher.

If an inert layer is combined with normal process conditions, the total average propylene production is increased and the catalyst is exposed to lower temperatures mainly in the upper part of the catalyst bed.

The invention claimed is:

1. An endothermic catalytic dehydrogenation process comprising:
    providing a catalyst bed system in a reactor, wherein the catalyst bed system comprises (1) a horizontal catalyst bed comprising a catalytic material and a first inert material, and (2) a layer of a second inert material of a predetermined volume arranged upstream of the horizontal catalyst bed, wherein the volume of the reactor above the second inert material is not filled by any solid material, wherein the ratio of volume of the second inert material to the volume of the reactor above the second inert material is between 0.04 and 0.73, and wherein the second inert material is selected from:
- (i) an oxide of a main group II element, an oxide of a main group III element, an oxide of a transition group III element, an oxide of a transition group IV element, an oxide of a transition group V element, and mixtures thereof,
- (ii) a nitride of a main group III element, a nitride of a main group IV element, and mixtures thereof, and
- (iii) a carbide of a main group III element, a carbide of a main group IV element, and mixtures thereof;

optionally contacting the catalytic material with a reduction gas to reduce the catalytic material;

passing a heat stream having a first temperature T1 through the volume of the second inert material and the horizontal catalyst bed, thereby heating the second inert material and the horizontal catalyst bed and regenerating the catalytic material; and subsequent to passing the heat stream through the volume of the second inert material, passing a hydrocarbon stream having a second temperature T2 through the volume of the second inert material and the horizontal catalyst bed, thereby dehydrogenating the hydrocarbon stream in the horizontal catalyst bed, wherein:
- (i) the second inert material is upstream of the horizontal catalyst bed for both the heat stream and the hydrocarbon stream,
- (ii) T1 is between 700 and 1000° C. and T2 is between 400 and 650° C., and
- (iii) T1>T3>T2, wherein T3 is a temperature at the interface of the second inert material and the horizontal catalyst bed which fluctuates by about 10 to 100° C.

2. The process according to claim 1, wherein the temperature T1 of the heat stream is between 725 and 810° C.

3. The process according to claim 1, wherein the temperature T2 of the hydrocarbon stream is between 550 and 650° C.

4. The process according to claim 1, wherein the temperature T3 is between 500 and 800° C.

* * * * *